US012702353B1

(12) United States Patent
Mirza et al.

(10) Patent No.: US 12,702,353 B1
(45) **Date of Patent: *Aug. 11, 2026**

(54) SYSTEM AND METHOD TO MEASURE PAIN LEVELS OF PATIENTS FOLLOWING SURGERY

(71) Applicants: Mary Hitchcock Memorial Hospital, for itself and on behalf of Dartmouth-Hitchcock Clinic, Lebanon, NH (US); The Trustees of Dartmouth College, Hanover, NH (US)

(72) Inventors: Sohail K. Mirza, Fairfax, VA (US); John B. Weaver, Hanover, NH (US)

(73) Assignees: Mary Hitchcock Memorial Hospital, for itself and on behalf of Dartmouth-Hitchcock Clinic, Lebanon, NH (US); The Trustees of Dartmouth College, Hanover, NH (US)

( * ) Notice: Subject to any disclaimer, the term of this patent is extended or adjusted under 35 U.S.C. 154(b) by 615 days.

This patent is subject to a terminal disclaimer.

(21) Appl. No.: 18/130,072

(22) Filed: Apr. 3, 2023

Related U.S. Application Data

(63) Continuation of application No. 16/779,556, filed on Jan. 31, 2020, now Pat. No. 11,617,536.

(Continued)

(51) Int. Cl.

| | |
|---|---|
| ***A61B 5/00*** | (2006.01) |
| ***A61B 5/01*** | (2006.01) |

(Continued)

(52) U.S. Cl.

CPC ............. *A61B 5/4824* (2013.01); *A61B 5/01* (2013.01); *A61K 9/14* (2013.01); *A61B 5/055* (2013.01); *G01N 33/543* (2013.01); *G01R 33/12* (2013.01)

(58) Field of Classification Search

CPC ......... A61B 5/4824; A61B 5/01; A61B 5/055; A61K 9/14; G01N 33/543; G01R 33/12

See application file for complete search history.

(56) References Cited

U.S. PATENT DOCUMENTS 6,885,192 B2 * 4/2005 Clarke ................ G01R 33/326 324/306

8,954,131 B2 2/2015 Weaver (Continued)

FOREIGN PATENT DOCUMENTS

KR 20180129468 A 12/2018

OTHER PUBLICATIONS

Simple and Portable Magnetic Immunoassay for Rapid Detection and Sensitive Quantification of Plant Viruses, Rettcher et al., Applied and Environmental Microbiology, May 2015 vol. 81 No. 9, pp. 3039-3048 (2015) (Year: 2015).*

(Continued)

*Primary Examiner* — Sean P Dougherty

(74) *Attorney, Agent, or Firm* — Loginov & Associates, PLLC; William A. Loginov

(57) ABSTRACT

This invention provides a non-invasive system for measuring pain level in a body at a site containing a predetermined concentration of magnetic nanoparticles. A drive coil and a pickup coil transmit and measure a field passing through the site based upon response of the magnetic nanoparticles, and a processor computes a pain level based upon variations in the field. The pain level can be indexed to an absolute scale that affords more predictability and objectivity in determining true pain level. Illustratively, the processor derives values for levels of cytokine IL-6, SP and temperature at the site, which are translated into the pain level. In an embodi- (Continued)

ment, the system and method can be implemented in a handheld device in which the drive coil and pickup coil reside in a housing.

19 Claims, 9 Drawing Sheets

Related U.S. Application Data

(60) Provisional application No. 62/799,094, filed on Jan. 31, 2019.

(51) Int. Cl.
*A61B 5/055* (2006.01)
*A61K 9/14* (2006.01)
*G01N 33/543* (2006.01)
*G01R 33/12* (2006.01)

(56) References Cited

U.S. PATENT DOCUMENTS

2005/0267569 A1* 12/2005 Barrett ..................... A61F 2/82 623/1.44
2008/0024117 A1* 1/2008 Hong ..................... G01N 27/74 324/201
2010/0081958 A1* 4/2010 She ..................... A61B 5/7232 327/344
2011/0074403 A1* 3/2011 Horng ................ G01R 33/1269 324/248
2011/0098558 A1* 4/2011 Weaver ............. G01R 33/4808 600/420
2014/0200626 A1 7/2014 Campbell
2016/0022976 A1* 1/2016 Peyman ............. A61K 47/6929 600/407
2016/0296145 A1* 10/2016 Bajaj .................... A61B 5/6824
2017/0000375 A1* 1/2017 Demas .................. A61B 5/145
2018/0049691 A1 2/2018 Nowosielski
2019/0008397 A1 1/2019 Fine
2020/0110085 A1* 4/2020 Weaver ................. A61B 5/055
2021/0138249 A1 5/2021 Howard
2021/0369630 A1 12/2021 Dobson

OTHER PUBLICATIONS

David W. Baker, MD, “History of The Joint Commission’s Pain Standards, Lessons for Today’s Prescription Opioid Epidemic”, JAMA, Mar. 21, 2017, viewpoint, vol. 317, No. 11, 1117-1118.
Hoopes et al., “In Vivo Imaging and Quantification of Iron Oxide Nanoparticle Uptake and Biodistribution”, Proc SPIE Int Soc Opt Eng, Mar. 23, 2012, 8317, 14 pages.
Perreard et al., “Temperature of the Magnetic Nanoparticle Microenvironment: Estimation from Relaxation Times”, Phys Med Biol, Mar. 7, 2014, 59(5) 1109-19.
Rauwerdink et al., “Simultaneous quantification of multiple magnetic nanoparticles”, Nanotechnology, Nov. 12, 2010, 21(45) 455101, 12 pages.
Reeves et al., “Magnetic nanoparticle sensing: decoupling the magnetization from the excitation field”, J Phys D Appl Phys., 2014, 47(4) 045002, 18 pages.
Weaver et al., “Measurement of magnetic nanoparticle relaxation time”, Med Phys, May 2012, 39(5) 2765-2770.
Weaver et al., “Quantification of magnetic nanoparticles with low frequency magnetic fields: compensating for relaxation effects”, 2013, Nanotechnology, 24 ,325502, 7 pages.
Wu et al., “Pain 1: Treatment of acute postoperative pain”, Lancet 2011, 377(9784) 2215-25.
Zhang et al., “Molecular Sensing with Magnetic Nanoparticles Using Magnetic Spectroscopy of Nanoparticle Brownian Motion”, Biosens Bioelectron, Dec. 2013, 50, 441, 15 pages.
Zhang et al., “Toward Localized In Vivo Biomarker Concentration Measurements”, IEEE Trans Magn., Feb. 2015, 51(2), 1-4.

* cited by examiner

SYSTEM AND METHOD TO MEASURE PAIN LEVELS OF PATIENTS FOLLOWING SURGERY

RELATED APPLICATION

This application is a continuation of co-pending U.S. patent application Ser. No. 16/779,556, entitled SYSTEM AND METHOD TO MEASURE PAIN LEVELS OF PATIENTS FOLLOWING SURGERY, filed Jan. 31, 2020, which claims the benefit of U.S. Provisional Application Ser. No. 62/799,094, entitled SYSTEM AND METHOD TO MEASURE PAIN LEVELS OF PATIENTS FOLLOWING SURGERY, filed Jan. 31, 2019, the teachings of each of which applications are expressly incorporated herein by reference.

FIELD OF THE INVENTION

This invention relates to systems and methods for non-invasively scanning regions of the body, and more particularly to systems and methods that employ nanoparticles to facilitate scanned results.

BACKGROUND OF THE INVENTION

Pain is common following all surgery, and it frequently persists following back surgery, leading to prolonged opioid use, repeat surgeries, severe disability and failed back surgery syndrome. Inflammation is a physiologic marker of pain. Local inflammation is necessary for normal wound healing, but inflammatory response is variable across individuals. In general post-operative pain is poorly managed, and one barrier to effective management of acute pain is the absence of objective measures. Precise measurements of inflammation at the surgical site can correlate with post-operative pain. In general, patient self-reporting of pain is also highly variable across individuals. Although survey-based pain and function measures have improved, self-reporting remains problematic because it is influenced by medical history, past pain experiences, behavioral and social factors, and it can vary over time. The problem is significant, in that over 30 million major operations are performed in the U.S. and one (1) annually for every 25 people worldwide. The ability to quantify pain measurements and correlate them to an absolute or substantially fixed scale of relative pain is, thus, highly desirable to increase and enhance positive outcomes of such surgeries.

SUMMARY OF THE INVENTION

This invention overcomes disadvantages of the prior art by providing novel technology for noninvasively monitoring local inflammation over time that could provide objective pain measurement at the surgical site. The system and method herein for determining pain can be applied to a patient in a straightforward manner with minimal discomfort. The system and method allow a practitioner to objectively measure post-operative pain. One exemplary area of treatment to which the system and method can be applied is back surgery. Surgical fields close to the skin surface can be read using portable units that could be sent home with patients. Deeper surgical fields can require a visiting nurse to read them out with portable equipment. In general, surgical fields in the center of the patient might require return trips to a clinic to read the probes. More particularly, the system and method entails objective measurement of post-operative (or other) pain using local inflammatory response (IL-6 concentration and temperature) and elevation of pain neurotransmitters (substance P (SP) concentration) at the surgical/wound site. Elevation in pain sensitivity induced by surgery/injury is proportional to the severity of tissue injury at the surgery site. Therefore, persistent post-operative pain can be distinguished from normal healing by persistent elevation of inflammation and pain biomarker measurements at the surgery site. Accordingly, longitudinal objective measurements of epidural temperature and concentrations of interleukin-6 (IL-6) and SP can correlate with post-operative pain following back surgery. The use of novel microscopic magnetic nanoparticle probes that can be safely implanted in the surgical field can allow for noninvasive postoperative measurements of precise local temperature and concentrations of these biomarkers using (e.g.) magnetic spectroscopy instrumentation to quantify Brownian Motion of nanoparticles tagged to target biomarkers (Magnetic Spectroscopy of Brownian Motion or MSB).

In an illustrative embodiment, a system and method for measuring pain level in a body at a site containing a predetermined concentration of magnetic nanoparticles is provided. A drive coil and a pickup coil transmit and measure a field passing through the site based upon response of the magnetic nanoparticles, and a processor that computes a pain level based upon variations in the field. Illustratively, the processor derives values for levels of cytokine IL-6, SP and temperature at the site. The drive coil and pickup coil can reside in a housing of a handheld sensing device, and/or the processor resides in the housing. The drive coil and the pickup coil can be arranged in a coaxial arrangement on a same side of the site, and/or the drive coil and the pickup coil can respectively be arranged at separate, remote locations relative to the site. The pickup coil can be arranged perpendicular to the drive coil, and/or it can be located adjacent to a DC coil. Illustratively, the pickup coil comprises a pair of pickup coils located on each of opposing sides of the site and the drive coil comprises a pair of drive coils coaxial with respective of the pickup coils.

BRIEF DESCRIPTION OF THE DRAWINGS

The invention description below refers to the accompanying drawings, of which.

DETAILED DESCRIPTION

I. General Overview

Figure 1:
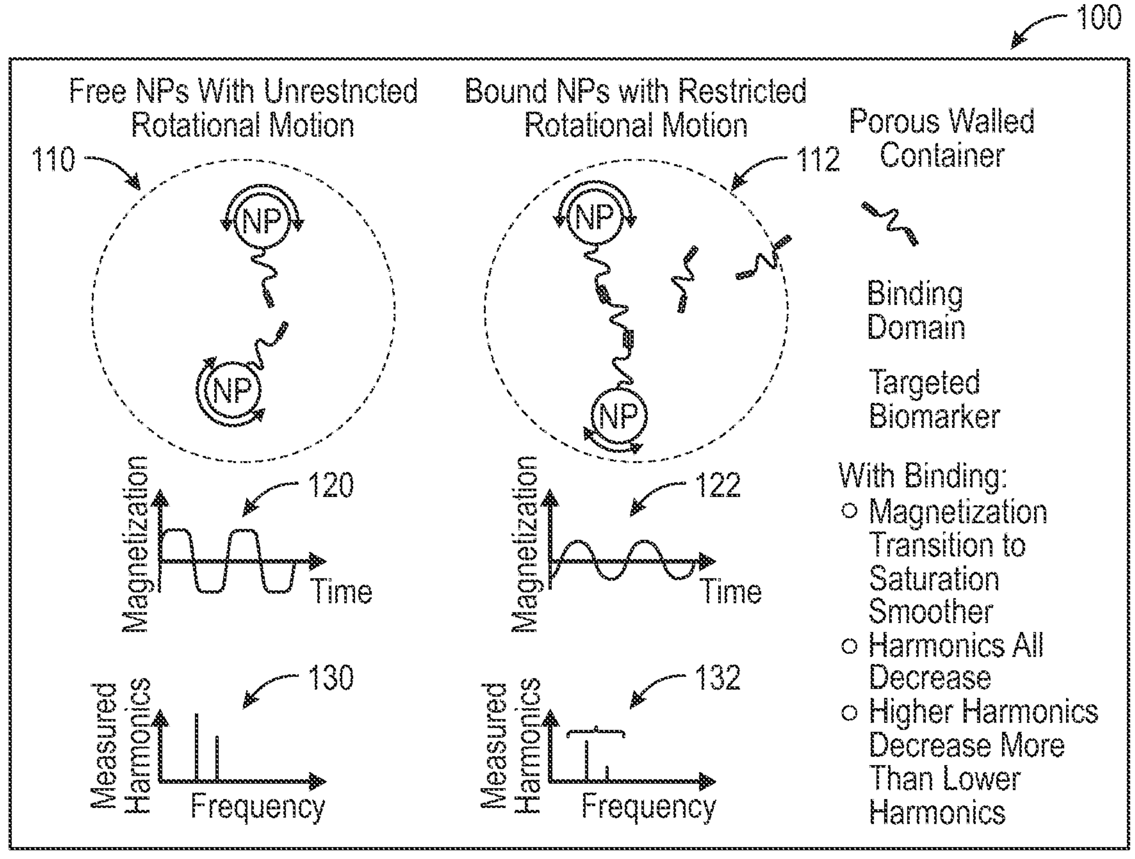
FIG. 1 is a diagram showing unbound versus bound magnetic nanoparticles (NPs) illustrating principles of the system and method herein.

The illustrative embodiment herein is directed, by way of non-limiting example to back surgery. This area of treatment is desirable to apply the techniques of the system and method given its frequency, cost, and the potential for poor outcomes. Precise tracking of inflammation and pain markers at the surgery site can provide objective measurement of post-operative pain. As described above, local inflammation is expected to allow for normal wound healing, but the degree of inflammatory response to injury is highly variable across patients. Inflammation from wound healing begins within hours and abates completely within a few days after surgery, when the proliferative phase of wound healing begins. Patient-specific immune states before surgery correlate with protracted recovery, including post-operative pain, fatigue, and functional impairment. Immune cell intracellular signaling in response to biomarkers, such as the cytokine Interleukin-6 (IL-6), has been shown to predict slower recovery and persistent pain following primary hip replacement surgery for osteoarthritis. It is noted that patients who have persistent local inflammation may be distinguishable from normal wound healing by monitoring the character and time course of local inflammation at the surgical site. Persistent pain may be associated with higher levels and longer duration of inflammation.

Reference is made to U.S. Pat. No. 8,954,131, entitled MAGNETIC PARTICLE IMAGING (MPI) SYSTEM AND METHOD FOR USE OF IRON-BASED NANOPARTICLES IN IMAGING AND DIAGNOSIS, issued Feb. 10, 2015, by John B. Weaver, et al., the teachings of which are incorporated herein by reference. This patent and related research therearound in Magnetic Spectroscopy of nanoparticle Brownian motion (MSB) allows the user to precisely measure local temperature and concentrations of biomarkers in vivo in a mouse model. See also, by way of useful background information, Weaver J B, Kuehlert E. *Measurement of magnetic nanoparticle relaxation time*, Med Phys 2012; 39 (5): 2765-70; Zhang X, Reeves D B, Perreard I M, et al., *Molecular sensing with magnetic nanoparticles using magnetic spectroscopy of nanoparticle Brownian motion*, Biosens Bioelectron 2013; 50:441-6; Weaver J B, Zhang X, Kuehlert E, et al., *Quantification of magnetic nanoparticles with low frequency magnetic fields: compensating for relaxation effects*, Nanotechnology 2013; 24 (32): 325502; Hoopes P J, Petryk A A, Gimi B, et al., *In Vivo Imaging and Quantification of Iron Oxide Nanoparticle Uptake and Biodistribution*, Proc SPIE Int Soc Opt Eng 2012; 8317: 83170R; and Perreard I M, Reeves D B, Zhang X, Kuehlert E, Forauer E R, Weaver J B, *Temperature of the magnetic nanoparticle microenvironment: estimation from relaxation times*, Phys Med Biol 2014; 59(5):1109-19. By way of background, the above-referenced developments consists of microscopic biocompatible probes filled with magnetic nanoparticles that can be placed in the surgical field just prior to closing, ensuring measurements reflect the local surgical site environment. The inventors have adapted MSB technology based upon a rat lumbar radiculopathy model and perform a proof-of-principle demonstration that time course of epidural temperature and concentration of inflammation and pain biomarkers provides objective metrics for surgical site pain. Based upon experimentation using the Rat model, it has been surmised that the use of MSB probes for pain measurement in human patients is feasible, and the technology has the potential to be rapidly translated clinically and accepted by surgeons. It is contemplated that pain measurements can be read out to surgeons and other practitioners (e.g. pain management professionals) with inexpensive systems that can be tailored to the task and capable of point-of-care application.

In general, the illustrative system and method adapts MSB instrumentation for longitudinal in vivo measurements of epidural temperature, cytokine Interleukin-6 (IL-6) concentration, and pain mediator substance P (SP) concentration in rats. Sensitivity of the apparatus can be optimized for epidural space MSB measurements of temperature, IL-6 concentration, and SP concentration. It is noted that measuring the character and time course of inflammation and pain biomarkers at the surgical site may provide objective pain measurement. Local inflammation is the earliest physiologic response to injury, and increased local cytokine concentrations occur in the earliest phase of the inflammatory process. Inflammation markers and pain mediators in normal healing peak within hours of an incision and slowly decrease as fibroblastic and granulation tissue forms. Prolonged local elevation of temperature and concentration of inflammation and pain biomarkers may be associated with persistent surgical site pain. Inflammation is necessary for normal wound healing, but the degree of inflammation and pain in response to injury is highly variable across patients. Patient-specific immune states before surgery correlate with protracted recovery. It is recognized that, immune cell intracellular signaling in response to biomarkers, such as cytokine Interleukin-6 (IL-6), predicts pain following hip replacement surgery. SP is a neuropeptide involved in pain perception. Local temperature is an early marker of inflammation, but local temperature measurements are expensive and cumbersome. Inflamed, painful joints show local temperature increase and elevated concentration of cytokines and SP.

Although it is desirable for normal wound healing, the degree of inflammation in response to injury is highly variable across patients, and preoperative immune states correlate with surgical recovery. Local concentrations of cytokines are significant for three reasons: (1) A local measure isolates the effect to the surgical site; (2) Many processes stimulate cytokine production: minor infections elsewhere in the body or a cold or even muscle contraction; and (3) A local measure from the surgical site should be more sensitive because cytokines are produced by immune cells at the site of injury, so the local concentrations will reach much higher levels than those after it is diluted in the blood volume. The inventors have recognized that expanding MSB measurements to include SP. It is recognized that the illustrative systems and methods of measuring molecular concentrations have potential for identifying inflammation and pain because (1) the concentrations measured are quantitative; (2) the concentrations measured are localized to the surgical site; and (3) sequential noninvasive measurements can be made over time. Persistent local temperature increase and elevated SP concentration in an inflamed joint is characteristic of persistent pain. Sequential measurements over time of inflammation and pain biomarker concentrations and local temperature may help distinguish normal wound healing from persistent post-operative pain.

The novel MSB systems and methods herein are capable of following local inflammation longitudinally in vivo in three ways: measuring the local cytokine concentration, measuring the local SP concentration, and measuring the local temperature. The technology development proposed in this application to measure the local IL-6 concentration and SP concentration and the local temperature can produce inexpensive, point of care technology that can be used both in the clinic during follow up visits and for home visits.

In an exemplary embodiment, the system and method can be particularly adapted to longitudinal in vivo measurements of epidural temperature, IL-6 concentration, and SP concentration to lumbar surgery. The sensitivity of the sensing apparatus can be optimized for epidural space MSB measurements of temperature, IL-6 concentration, and SP concentration in this region of the body. With reference particularly to the diagram of FIG. 1, the system and method can be optimized from experiments entailing in vivo use in a rat model of lumbar spine surgery to quantitatively compare the in vivo MSB IL-6 and SP measurement with ELISA on epidural tissue. The diagram 100 depicts the physics of MSB measurement of concentration. When NPs in the porous probe are not bound (110) they rotate freely to align with the applied field. Saturation produces sharp transitions in the temporal magnetization producing signals at higher harmonics (graphs 120 and 130). When the targeted analyte is present (112), it binds NPs together, reducing their rotational freedom and the speed with which they align with the applied field, thus rounding the sharp transitions in the magnetization and reducing the harmonics (and the ratio of the harmonics) (graphs 122 and 132). The more the NPs are bound, the lower the ratio of harmonics, which provides a measurement standard for the apparatus. Note that tissue measurements are contaminated with intracellular IL-6 and are subject to localization errors, both of which can be controlled by consistently sampling to dura and a thin layer of epidural muscle the L5 laminectomy site. The MSB measure of epidural temperature will be validated against a telemetry sensor at the same location.

Note that a particular advantage of the present system and method relates to limitations in current methods of measuring in vivo cytokine and SP concentrations that is, currently biopsy is the only way to measure the local cytokine and SP concentration. Serum cytokine levels have been used since the 1980's as effective early markers for systemic infection, but are unable to isolate local inflammation because of dilution and uncertain origin. Biopsy is simply not practical for longitudinal surgical wound surveillance; patients would not accept it and the side-effects including risk of introducing iatrogenic infection and contusion cannot be justified.

Figure 2A:
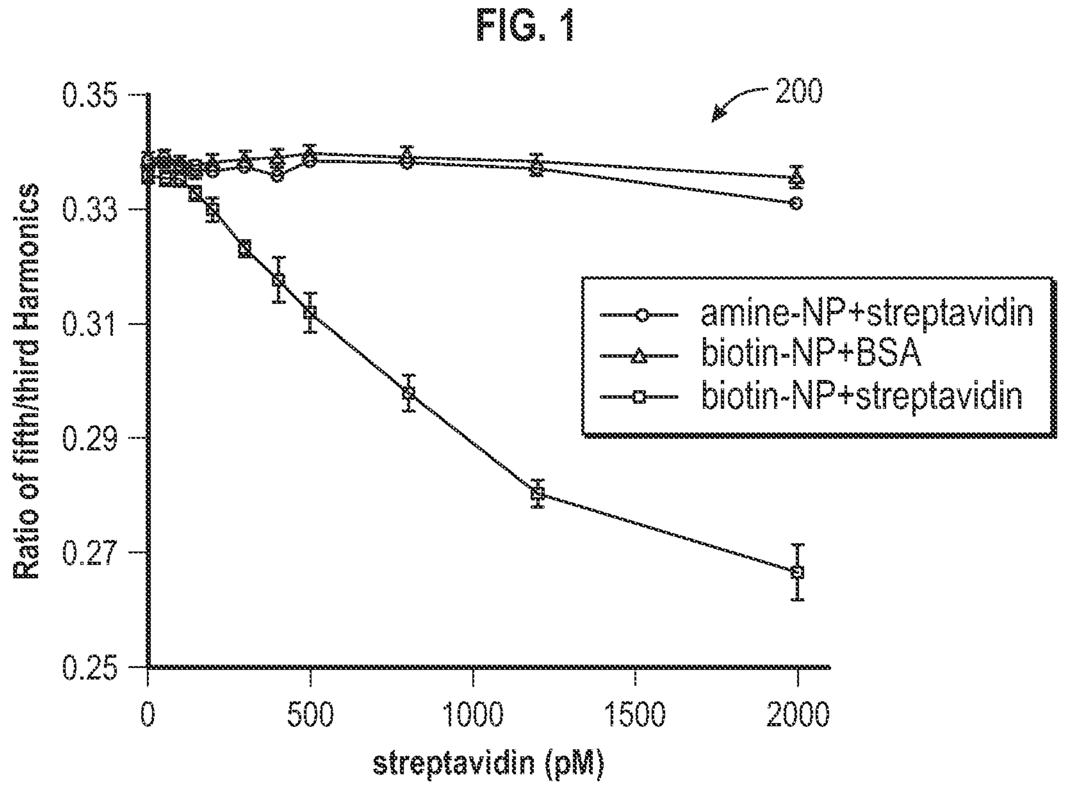
FIG. 2A is a graph showing measured harmonic ratio as a function of streptavidin concentration using an experimental version of the sensing apparatus of the system and method.
Figure 2B:
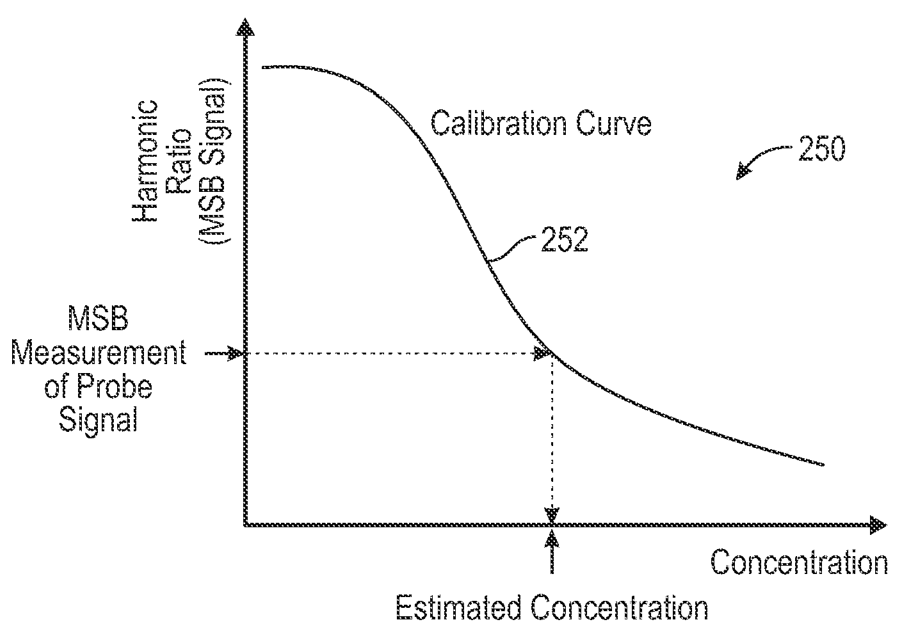
FIG. 2B is a graph showing that the harmonic ratio drops monotonically with increasing analyte concentration.

Brief reference is made to FIGS. 2A and 2B, by way of further background. The graph 200 of FIG. 2A shows measured harmonic ratio as a function of streptavidin concentration using an experimental version of the measurement apparatus. The sensitivity, or minimum detectable concentration of streptavidin is 200 μM. Two controls exist: NP without biotin and with BSA. FIG. 2B is a graph 250 showing that the harmonic ratio drops monotonically with increasing analyte concentration so each ratio corresponds to one analyte concentration allowing the concentration to be estimated from a single harmonic ratio. The stability of the solution can be improved by assuming a functional form for the calibration curve 252.

Figure 3:
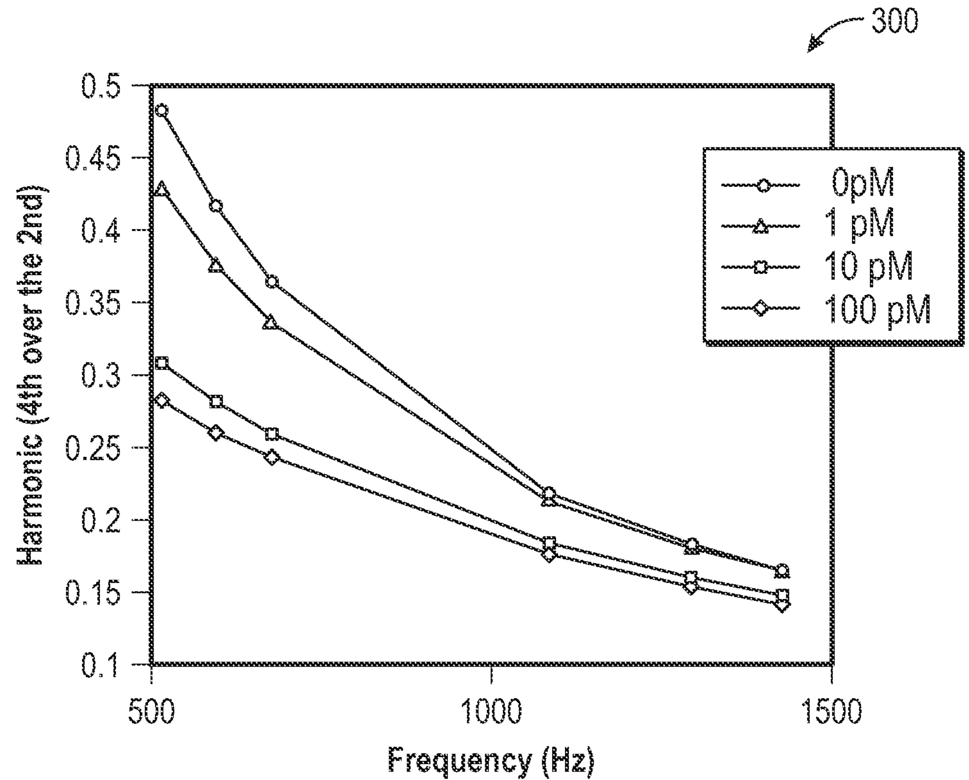
FIG. 3 is a graph showing MSB spectra acquired with the experimental version of the sensing apparatus in which the apparatus' pickup coil perpendicular to the applied field supplied by the driver coil.
Figure 4:
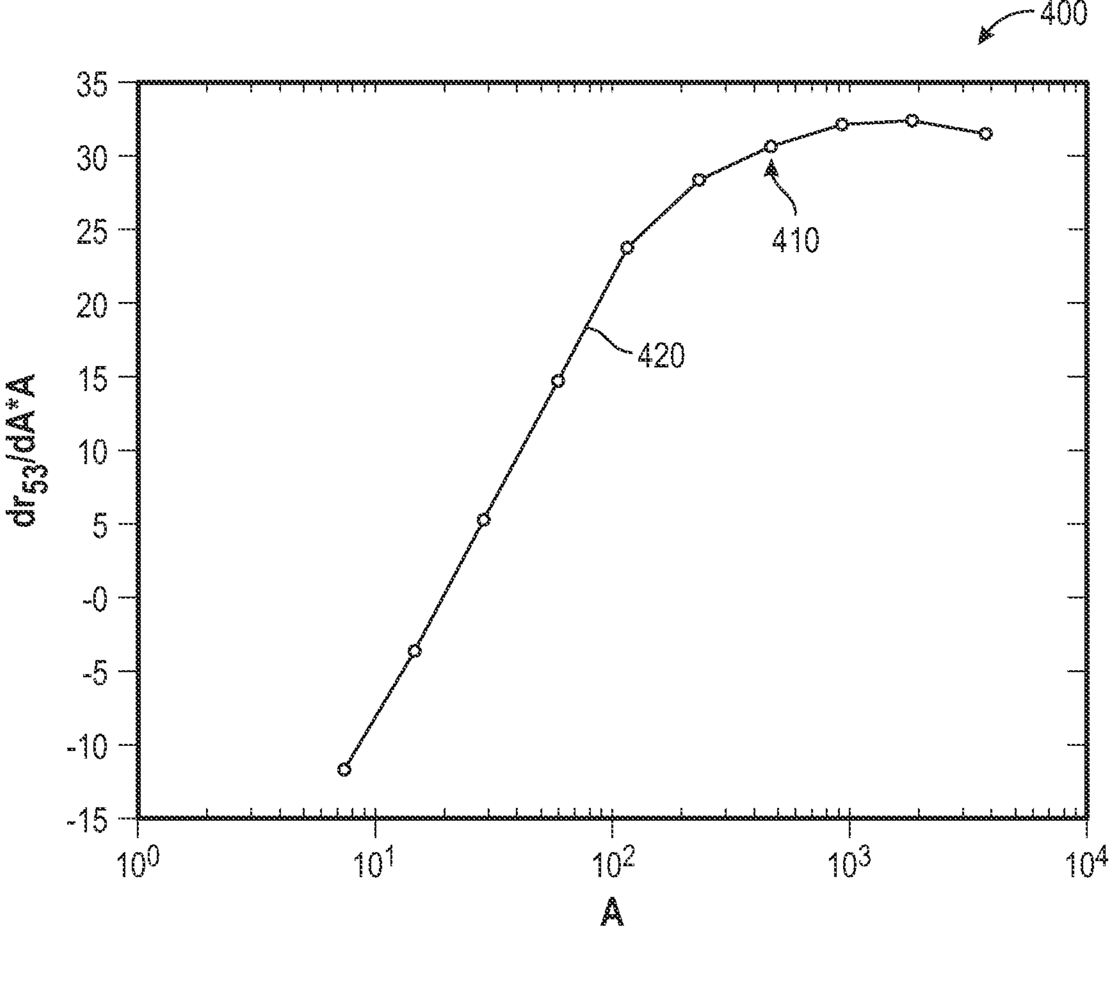
FIG. 4 is a graph of an illustrative Langevin equation, used to model the magnetization of NPs associated with the system and method.

FIG. 3 is a graph 300 of MSB spectra acquired with the current experimental version of the measurement apparatus with the pickup coil perpendicular to the applied field for 1 μM, 10 μM, and 100 μM of IL-6, compared with a control with no IL-6. The standard deviations obtained from each measurement are shown to the right of the plotted points. The p-values comparing the spectra with the control were calculated using previously published methods (see Wu C L, Raja S N, *Treatment of acute postoperative pain*, Lancet 2011; 377(9784): 2215-25; and Baker D W, *History of The Joint Commission's Pain Standards: Lessons for Today's Prescription Opioid Epidemic*, JAMA 2017; 317(11):1117-8.), and were zero to computational accuracy for all concentrations of IL-6. Substantially lower concentrations can be measured and the inventors have obtained preliminary data suggesting 1 fM concentrations can be measured. Additionally, FIG. 4 shows a graph 400 of a Langevin equation, a stochastic differential equation, which has been employed to model the magnetization. It has been recognized that a useful closed-form approximation is the Langevin function of a single composite variable $\mathcal{A}=(\mu H)/(kT\omega\tau)$. The approximation allows the sensitivity (the derivative of the magnetization with respect to the relaxation time) to be estimated. A simulation was accomplished for Micromod NPs. The peak sensitivity is at the shoulder 410 of the harmonics curve 420 ($\mathcal{A}=1000$). By way of background, the experimental apparatus is adapted to operate at approximately $\mathcal{A}=200$ to 500, (e.g.) the separation between the signal with and without IL-6 in the graph 300 of FIG. 3 is larger for lower frequencies (larger $\mathcal{A}$). Thus, the sensitivity can be enhanced herein by increasing the amplitude or decreasing the frequency. The signal also increases with higher frequency so that higher frequencies and even higher amplitudes to increase $\mathcal{A}$, should improve the sensitivity. Numerical estimates suggest that at least a factor of ten is possible. This relationship can be employed in a version of the apparatus for measuring e.g. lumbar surgery pain levels.

II. Experimental Arrangement

Figure 5A:
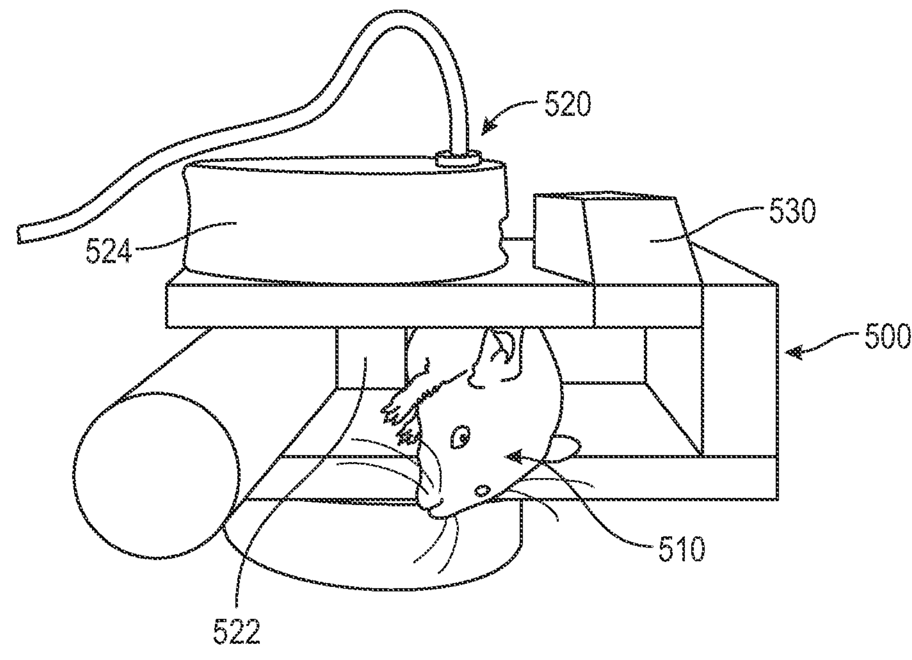
FIG. 5A is an illustration of the experimental version of the sensing apparatus with a perpendicular coil arrangement placed around a mouse that has been infused with NPs.
Figure 5B:
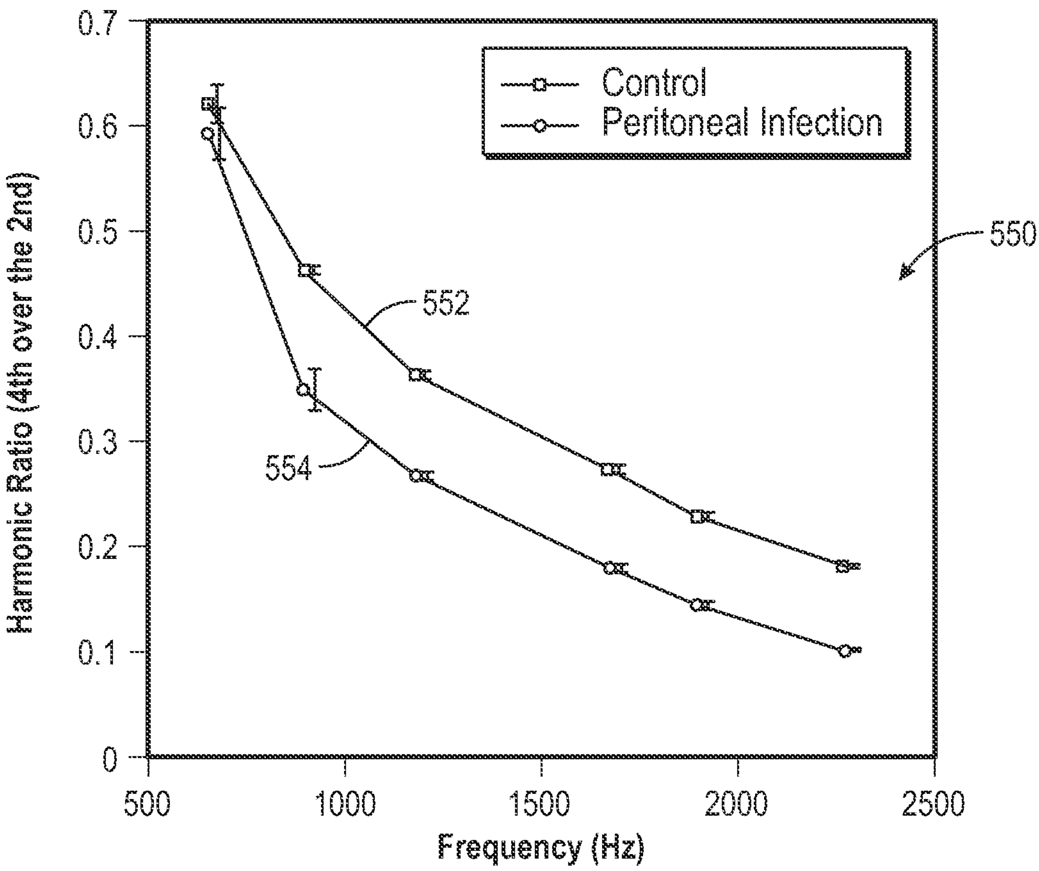
FIG. 5B is a graph showing in vivo measurements of increased IL-6 in the peritoneum a mouse using the apparatus of FIG. 5A with peritoneal bacterial infection versus a control mouse free of such infection.
Figure 6:
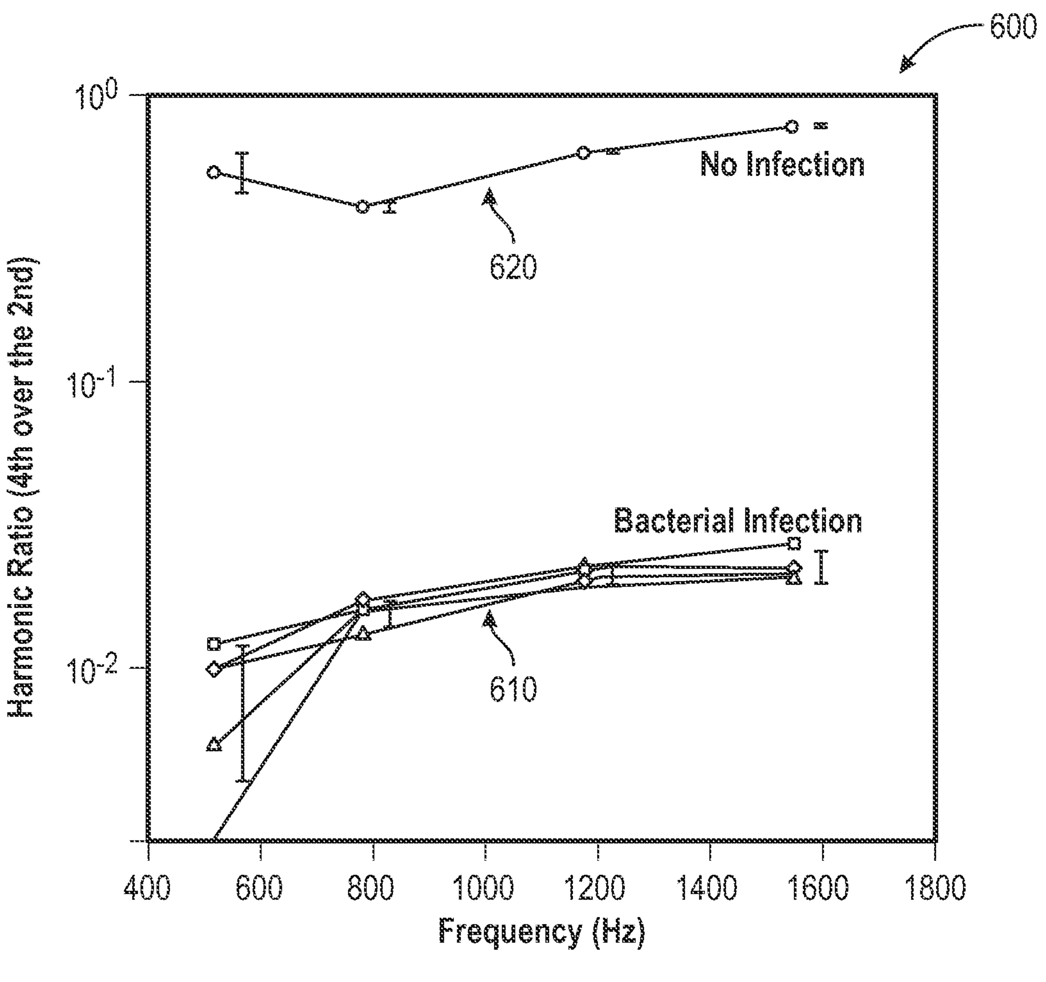
FIG. 6 is a graph showing MSB spectra from measurement of NPs with the experimental version of the apparatus of FIG. 5A, showing IL-6 concentration differences resulting from the above-described peritoneal infection.

Existing methods of measuring molecular concentrations shown in FIG. 1 can be optimized during experimentation with a current version of the apparatus for in vivo use in rats (See, by way of example, FIGS. 5A, 5B and 6). Probes formed of hollow, porous shells (200 μm or larger) are filled with NPs targeted in such a way that an analyte molecule binds two NPs together changing the MSB signal and allowing the bound fraction to be estimated. Concentrations of IL-6 have been measured in vitro (see the graph 300 of FIG. 3) and in vivo (FIGS. 5A, 5B and 6) for peritoneal cavity infection.

As shown in the depiction 500 of FIG. 5A a living, female C5 wild-type mouse 510 is mounted in an experimental version/arrangement 520 of the MSB in vivo measurement system. The system consists of a pickup coil 522 located adjacent to the mouse's abdomen and a drive coil 524 located above the mouse 510 as shown. A field monitoring coil 530 is located outside the arrangement of pickup and drive coils 522, 524, as shown in FIG. 5A, for measurement and control purposes in this example. The coils 522 and 524 are oriented in a perpendicular geometry with respect to each other in this arrangement 520, but can be oriented in other ways as described below. The arrangement 520 yields experimental results shown in the graph 550 of FIG. 5B. That is, preliminary in vivo measurements of increased IL-6 in the peritoneum of mice with peritoneal bacterial infection generate very high concentrations of IL-6 within hours of infection. The depicted female C5 wild type mouse 510 was infected with an IP injection of *Pseudomonas aeruginosa*, strain PA14 bacteria. A previously measured control mouse (not shown) had no infection. During experimentation, six hours following injection, 75 μL of IL-6 targeted Micromod 113 nm NPs were injected IP and 4 MSB spectra were measured 10 minutes later. The average spectra are plotted in two curves 552 and 554 of the graph 550, with the sample standard deviation shown beside. Clear separation of the two spectra occurs where the spectra from the infected mouse (curve 554) are lower than those from the control mouse (curve 552), as expected; the p-value is zero to computational accuracy. FIG. 6 further depicts graphs 600 showing MSB spectra from probes showing IL-6 concentration differences resulting from peritoneal infection. Probes filled with IL-6 targeted NPs were injected into the peritoneal cavity of five mice with bacterial infection (bottom curves 610) and the peritoneal cavity of a mouse with no infection (top curve 620). The MSB measurements were taken four hours after the bacteria were injected. The standard deviations of on the averages are shown slightly to the right of the points so they can be seen. The standard deviations for the infected mice are the sample standard deviations (representing the sum of the apparatus and animal uncertainties). Those for the uninfected control are the standard deviations from repeated measurement of the same animal (representing apparatus uncertainties). The p-value is zero to computational accuracy.

The experimental in vitro measurements with the arrangement 520 of FIG. 5A have demonstrated far higher sensitivity than should be required for measurement of pain levels—as high as single-digit fM can be measured and most cytokines reach 1 to 5 μM concentrations and IL-6 reaches 1 nM with infections. The first in vivo measurements (according to FIGS. 5A, 5B and 6) show infection with very high significance. Both the probes in FIG. 1 and the apparatus can be optimized as described in accordance with the curve 420 FIG. 4.

In further arrangements, probes are optimized for in vivo applications. The semipermeable nature of alginate microshells facilitates rapid exchange of small molecules while excluding large immune molecules. The probe's porous shell has been optimized for the pore size (to allow IL-6) and stability. In a current experimental arrangement, multiple thin layers of alginate are employed. The effective pore size is 12-16 nm. The shells are formed by injecting a mixture of NPs and Ca solution into alginate. The layer thickness is controlled by the time in alginate and the size by the injection pressure. The mechanical strength can be increased by increasing alginate concentration or by using other crosslinkers such as Ba2+. The porosity can be reduced by coating with additional polyionic layers—e.g., coating with poly-L-lysine (PLL) (~45 kDa117) or poly(ethyleneimine) or poly(acrylic acid). Chitosan modification of alginate microcapsules also enhances their mechanical strength and reduces the effective porosity allowing selectable cutoff between 15 kDa to 200 kDa. PEG can lower the cutoff to ~18 kDa. The speed with which the MSB signal changes with increasing IL-6 concentration is used as the metric for the porosity of the alginate shell surrounding the NPs. The above-described techniques can be adapted to the rat spine model, and thereby used to experimentally optimize probes for epidural measurements in humans and other mammalian lifeforms.

In various implementations of the current system and method probes are optimized. This optimization relates to the probe container structure, the NP size, the stiffness of the bonds with the analyte and the NP coating for in vivo applications. The semipermeable nature of alginate microshells facilitates rapid exchange of small molecules while excluding large immune molecules. Chitosan modification of alginate microcapsules also enhances their mechanical strength and reduces the effective porosity allowing selectable cutoff between 15 kDa to 200 kDa. PEG can lower the cutoff to ~18 kDa. The MSB signal changes will be used as the metric for the porosity of the alginate shell. Current experimentation has achieved very high sensitivity in vitro (as high as 4 fM of IL-6). However, the in vivo sensitivity of the system and method can be further optimized by developing a better understanding of the physical mechanisms that dominate the NP dynamics.

The approximations of NP performance can be enhanced by providing a more sensitive version of the arrangement. Those of skill can recognize that use of a Metglas core to generate the applied field and a very sensitive magnetometer (e.g. one commercially available from QuSpin Inc. of Louisville, CO.) can enhance performance. A larger applied field can allow for optimization of the MSB signal difference and the more sensitive magnetometer can deliver significantly higher sensitivity. Preliminary calculations suggest that the sensitivity can be improved by at least one to two orders of magnitude so the curves in FIGS. 5B and 6 will display significantly improved SNR.

The NP geometry can also be optimized to achieve better sensitivity in epidural tissue. A basic model can be obtained by calculating the population of linked NPs using Boltzmann equilibrium arguments but can be extended to full Langevin equation simulations 120, 128 if necessary. Preliminary data suggests that shorter links are better. The size of the two NPs can be varied to optimize the signal. The procedure can include conjugation of the IL-6 aptamers to the following combinations of (commercially available) Ocean and Micromod NPs: [Micromod 100 nm-Micromod 100 nm], [Ocean 20 nm-Micromod 100 nm], [Ocean 20 nm-Ocean 20 nm]. Sufficient quantities of NPs will be used to achieve the same signal as 5 μL of Micromod 100 nm NPs. PBS will be added to achieve a 200 μL sample volume. The change in harmonic ratio with addition of IL-6 to achieve 100 μM concentration will be measured. The NP sizes producing the smallest cumulative p-value 129 can be used. The largest NP sizes are expected to produce the largest differences for the range of frequencies currently used; higher frequencies should require smaller NPs.

The depicted arrangement 520 (FIG. 5A) can be further optimized (e.g. an improvement in sensitivity by a factor of 100, using various techniques described in the literature, including those described in Zhang X, Reeves D, Shi Y, et al., *Toward Localized In Vivo Biomarker Concentration*

*Measurements*, IEEE Trans Magn 2015; 51 (2): 1-4; and Reeves D B, Weaver J B, *Magnetic nanoparticle sensing: decoupling the magnetization from the excitation field*, J Phys D Appl Phys 2014; 47 (4): 045002.

In operation of the arrangement 520, it is recognized that there are two primary sources of noise, namely vibration and heating. The drive coil(s) 524 vibrate (both the entire assembly and individual wires with the assembly) creating noise in the pickup coil 522. Vibration can be reduced, in part, by employing stiffer materials in the construction of coils, etc. The second source of noise is drift caused by heating of the detector over time. Hence, in the present arrangement the drive coil's heat but that is compensated for using the field monitoring coil 530, the feedback from which is used to adjust the current in the drive coils to produce the desired field. However, the drive coil's also heat the detector slightly which biases the signal. Use of better insulating materials to avoid unwanted heating of components is desirable in further embodiments. By way of example, a Metglas iron core can be used to generate the drive field and the pickup coil can be physically isolated from the drive coil assembly. The weight of the iron core will reduce vibration substantially. The very large thermal mass of the core will also reduce heating of the pickup coil substantially. Use of (e.g.) a QuSpin magnetometer, instead of a pickup coil, can also reduce the frequency and increase the sensitivity. The sensitivity to iron can be used as the metric to evaluate the effectiveness of each of the proposed changes and assist in optimization of the system's design. The detectable amount of iron is a metric that can also be used to optimize the system used for in vivo measurements of NPs.

Figure 7A:
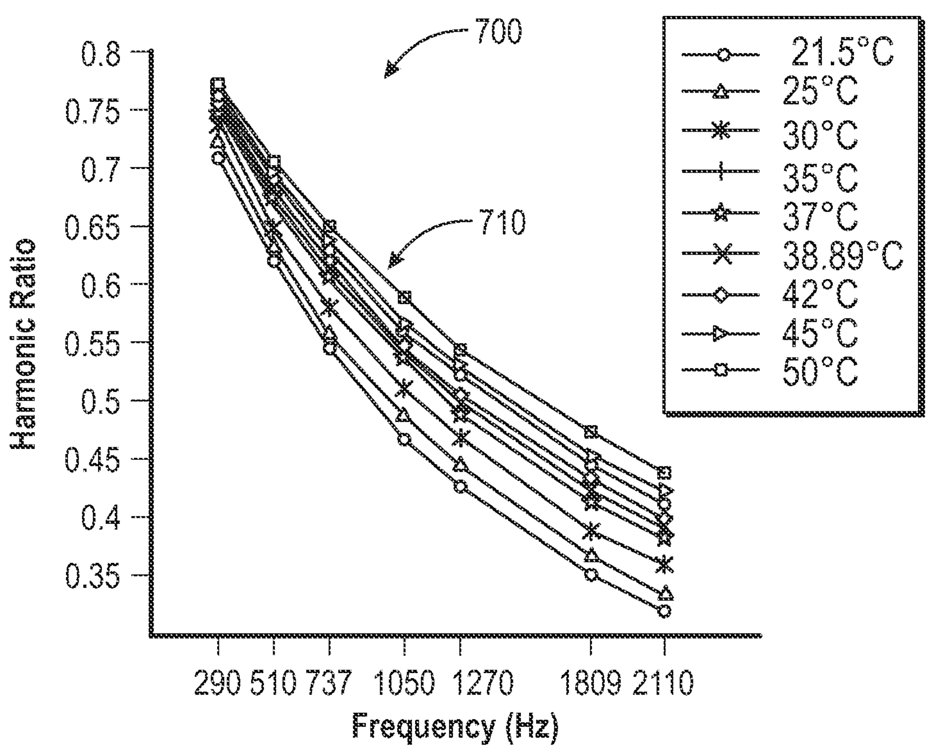
FIG. 7A is graph showing the harmonic ratios of a NP sample as a function of frequency at a range of temperatures
Figure 7B:
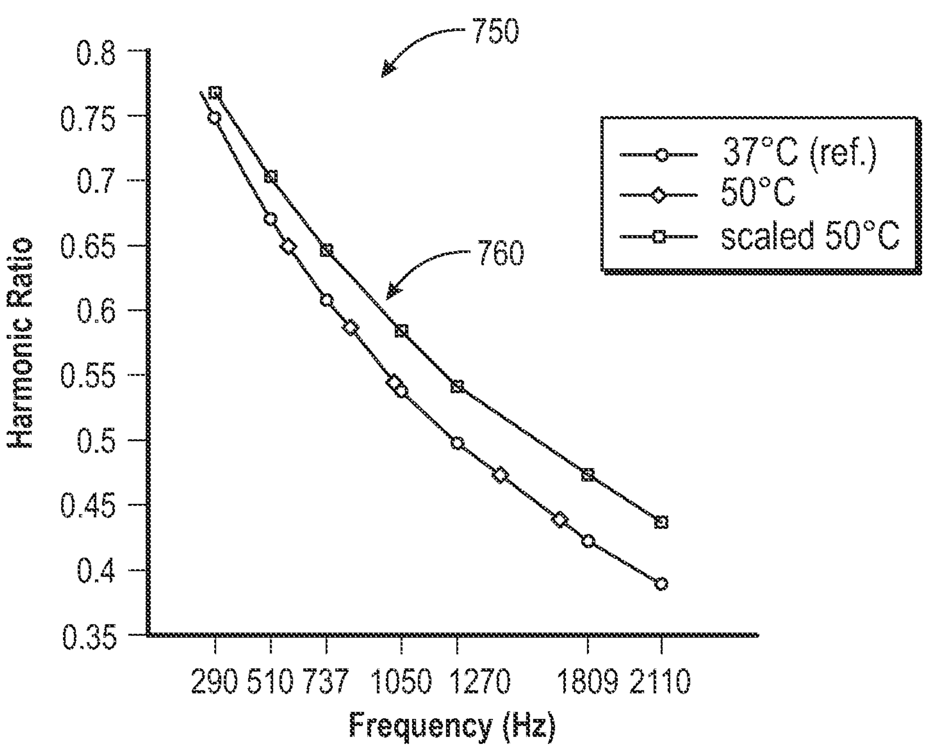
FIG. 7B is a graph showing an example of scaling the harmonic ratios of FIG. 7A with the relaxation time for two temperature values.

In the depicted arrangement 520, temperature of the treatment area can be measured using nonporous shells filled with untargeted NPs. Brief reference is made to the graphs 700 and 750 of FIGS. 7A and 7B. The graph 700 (FIG. 7A) shows curves 710 of the harmonic ratios of a NP sample as a function of frequency at a range of temperatures from 21.5° C. to 50° C. The graph 750 shows curves 760 of an example of scaling the harmonic ratios with the relaxation time for two temperature values, 37° C. and 50° C. The scaling allows the current temperature to be accurately calculated from a reference spectra at a known temperature with 0.87% error. The probes can be optimized for higher frequency temperature measurement using the relaxation time, and separately for lower frequency temperature measurement using the effective field. The two methods can be compared for robustness and accuracy in vitro to provide a preferred measurement standard. The change in signal for an incremental change of one degree at body temperature can be used as the metric. The temperature of the probes in this experimental arrangement can be controlled by water pumped around them from a large tank. The water temperature can be correlated to the MSB measurement. When optimized, MSB temperature readings are compared in vivo from MSB to readings from implanted telemetry sensors in the epidural space and body core. In operation, MSB should show strong correlation and agreement with the reference standards.

In an arrangement that combines IL-6, SP and temperature measurement, the arrangement can employ probes with different sizes of NPs, so as to measure temperature, IL-6 and SP concentration simultaneously/concurrently. The signal for each size of NP can be isolated using existing techniques—for example, those described in Rauwerdink A M, Giustini A J, and Weaver J B, *Simultaneous quantification of multiple magnetic nanoparticles*, Nanotechnology 2010; 21 (45): 455101. Relaxation of each size can allow the concentration and temperature to be measured with the same probe at the same time.

It is contemplated that the arrangement can result in increased temperatures at the sensed site that can potentially limit performance. If the increased temperature eliminates the effects of increased IL-6 and SP in the concentration measurements of the sensing arrangement, then at least two alternate implementations can be provided. The first implementation entails the use of lower frequencies, typically where the effects of binding are largest and the effects of temperature are smallest. The second entails sensing both the temperature and concentration using measurements over a range of frequencies and amplitudes of the applied magnetic field. The fact that increasing temperature effects are largest at higher frequencies5 and increased binding effects are largest at lower frequencies suggests that the two effects are independent, and can be solved using a sufficiently large range of applied fields which our new apparatus will be capable of providing. It is contemplated that a SERF magnetometer can also be employed to increase sensitivity.

III. Human-Based System and Method

Figure 8:
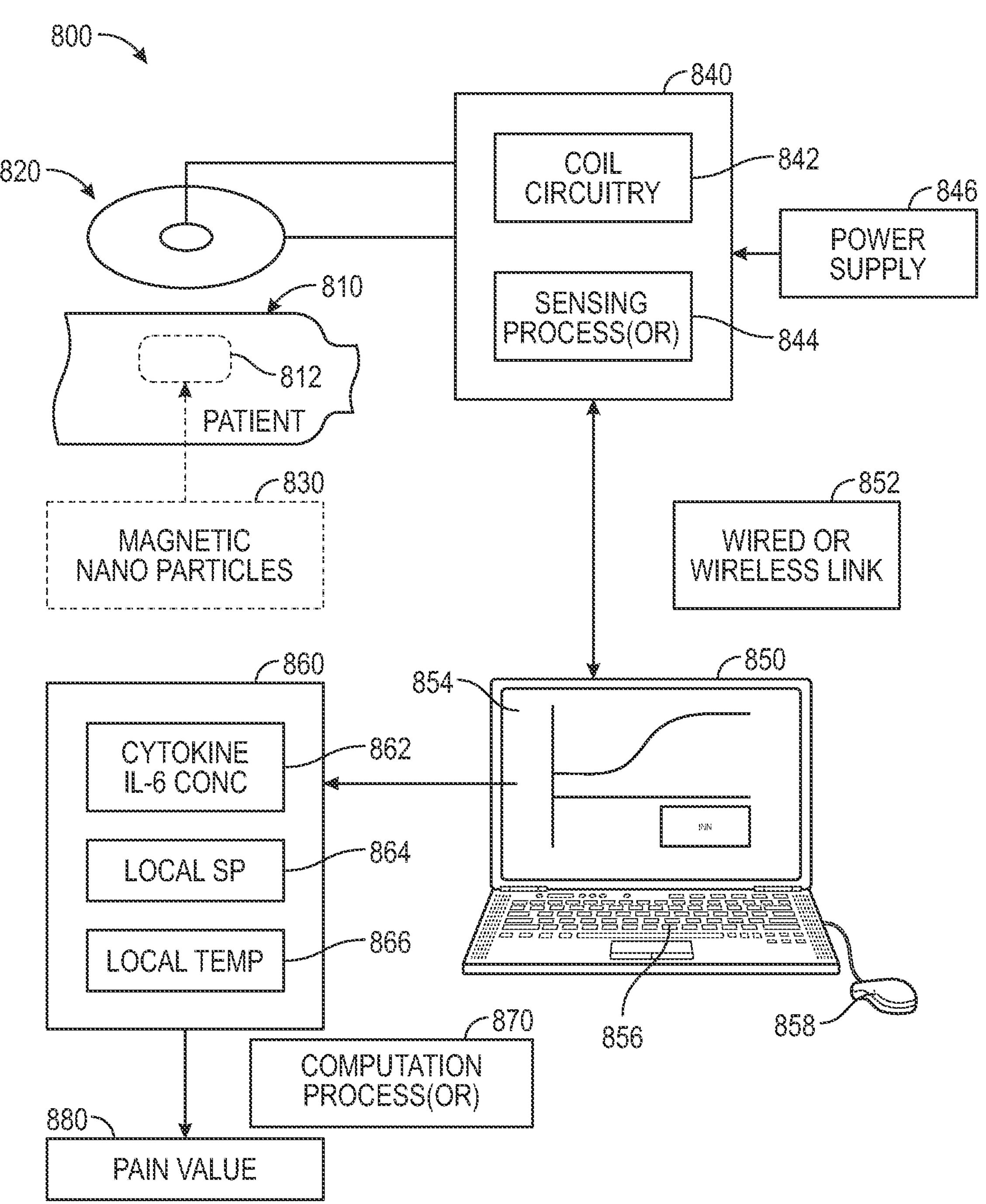
FIG. 8 is a diagram showing an arrangement of a system and method for sensing pain levels in a (e.g.) human patient at a treatment/wound site, including generalized circuitry and interface therefor.

Reference is now made to FIG. 8, which depicts an arrangement or device 800 for measuring and quantifying relative pain level at a wound or treatment site 812 of a patient 810. The depicted site 812 is along the spine in this example, but can be at another location that is close to, or more deep within the patient's body. The arrangement 800 includes a sensing assembly 820, consisting of a central pickup coil 822 and a relatively coaxial outer drive coil 824. Note that the term "pickup coil" as used herein can broadly refer to other types of devices that are capable of reading flux in magnetic fields generated by a drive coil (or other magnetic field generator), such as a magnetometer as described above. This particular assembly generates field lines between the coils 822 and 824 that remain relatively shallow, and thus, this assembly 820 is most suited to measure pain that is close to the skin surface of the body.

The wound or treatment site 812 have been infused with subcutaneous nanoparticles (NPs) 830 in sufficient concentration to generate a readable signal at the pickup coil 822. The particles can be deposited in solution (e.g. a colloidal solution, collagen, etc.), that allows them to remain sufficiently localized for a period of time. They can be delivered by a hypodermic needle or deposition using (e.g.) a dropper prior to surgical closure.

The coil assembly 820 is interconnected to a local or remote circuitry module, which can consist of various electronic hardware and software. In general, there is a coil circuit 842, which modulates current to the driver coil 824, and a sensing circuit or process (or) 844 that receives signals from the pickup and generates a usable signal representative of the telemetry desired to compute various telemetry. The circuit 840 is powered by a remote and/or local power supply (e.g. batteries, wall current, etc.) 846.

The circuit 840 delivers data derived from the sensing process (or) 844 to a local or remote computing device 850 via a wired and/or wireless link 852. The computing device can be any software/firmware-based processor, including but not limited to, a local processor (e.g. an FPGA or microprocessor within the sensing device housing), a laptop, PC, server, tablet or smartphone. The depicted, remote computing device 850 includes a user interface having a display and/or touchscreen 854, keyboard 856 and mouse 858. The display allows a user to enter settings information to operate the device and to view and manipulate data related to device function and pain measurement. Various communications systems (e.g. WiFi) can also allow the device to transmit data to a remote server for storage and analysis by a practitioner. Among other data, the computing device 850 generates data values 860 related to the patient site's cytokine IL-6 level 862, local SP 864 and local temperature 866 based upon operation of the sensing assembly 820. These values are provided to a computation process (or) 870, which applies operates appropriate equations and/or compares the values to stored statistics (e.g. a table lookup) to generate a relative pain index value 880 that can be displayed to the user and/or stored with an appropriate timestamp and/or other relevant data about the patient and system.

Figure 9:
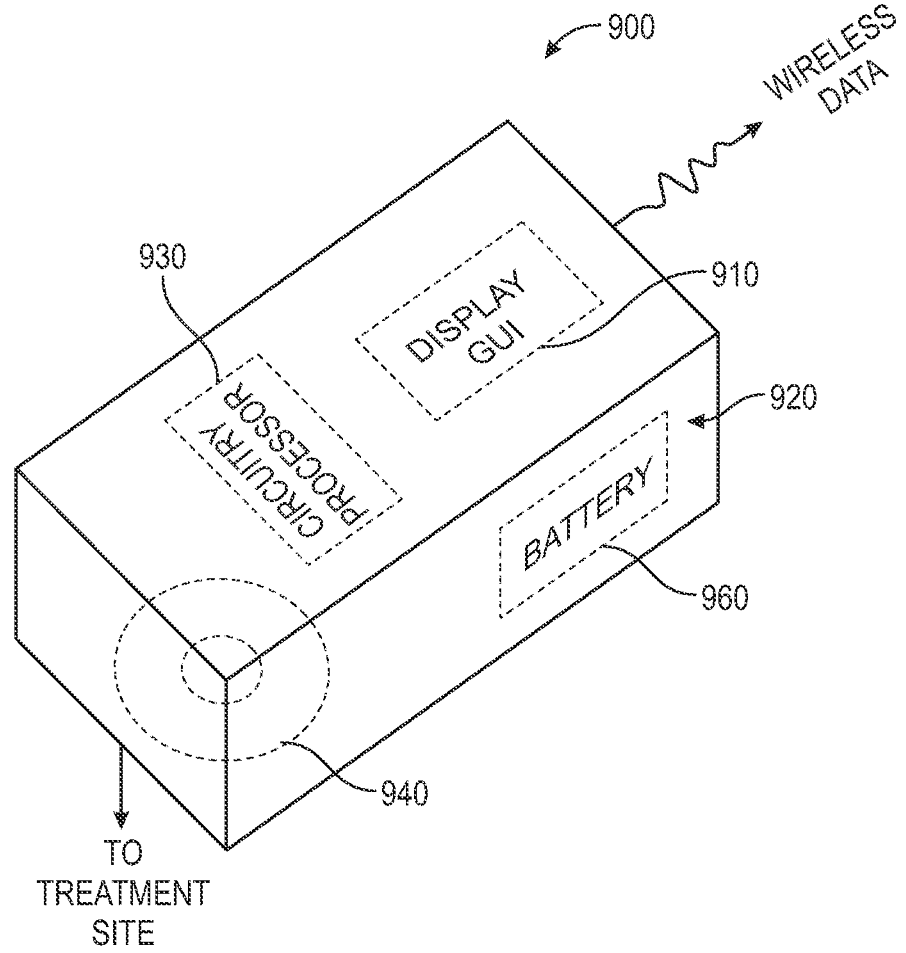
FIG. 9 is a diagram showing a handheld version of the arrangement of FIG. 8, typically employed for sensing NPs at relatively shallow depths within the patient's body.
Figure 10:
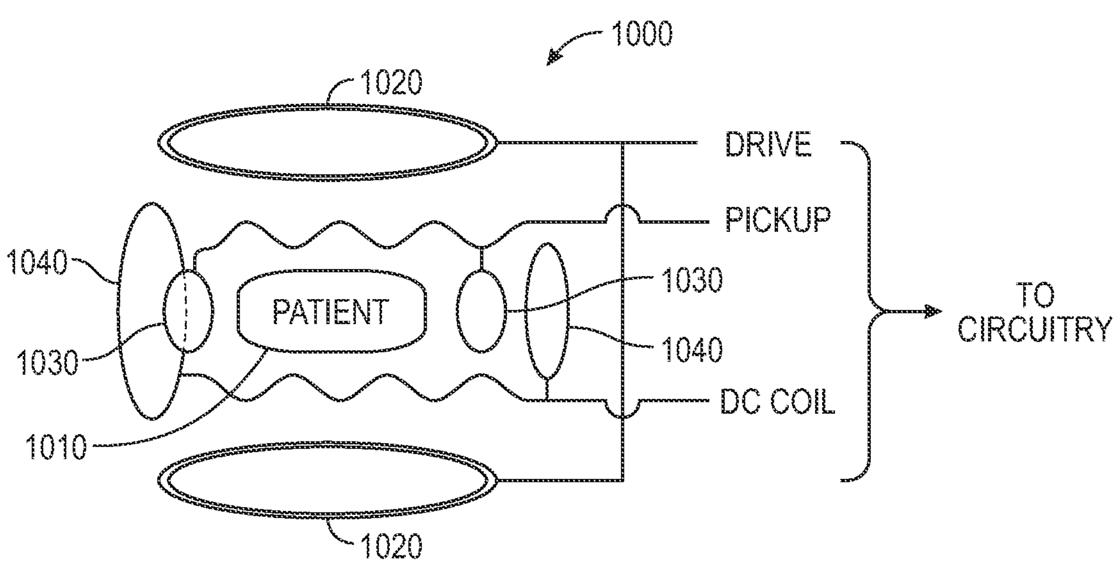
FIG. 10 is an embodiment of the system and method of FIG. 8, in which the driver and pickup coils thereof are arranged at a perpendicular orientation for sensing NPs at relatively deep locations within the patient's body.

FIG. 9 is a diagram of a handheld sensing device 900 in accordance with the arrangement 800 of FIG. 8. As shown, the device includes a display or graphical user interface (e.g. GUI touchscreen) 910 that can perform some or all of the functions of the above-described computing device 850. Alternatively, the handheld sensing device 900 can be piggybacked with a conventional processor and/or communication device, such as a tablet or smartphone (not shown). The GUI 910 and/or conventional computing device can be linked wired and/or wirelessly to the control and processing circuitry 930 within the housing 920 of the device 900. A coil assembly 940 as described in the arrangement of FIG. 8 (or another appropriate arrangement) generates a field that passes through the treatment/wound site of the patient and excites NPs and reads their response signal. An on-board power supply (e.g. battery(ies) 960) and/or wall-current transformer is also provided in the housing 920.

Where the treatment/wound site is too deep within the patient for a self-contained driver and pickup coil assembly (as described in FIGS. 8 and 9), the sensing assembly can be modified so that the patient is interposed between the driver and pickup coils. This arrangement can be implemented by applied coils (e.g. using straps, adhesives, etc., or a magnetically transmissive table. One such arrangement 1000 is shown in FIG. 10. As shown, the patient 1010 resides (relatively immobilized) between a pair of drive coils 1020. A pair of perpendicular pickup coils 1030 are provided along each side of the patient, intersecting the deep treatment/wound site. The pickup coils 1030 are coaxial with DC coils 1040 that enhance and direct the field lines between coils. The drive, pickup and DC coils 1020, 1030, 1040 are interconnected with appropriate sensing and control circuitry as described generally above (FIG. 8). The parameters of the coils can be adjusted manually and/or automatically (e.g. using step adjustments and feedback) to obtain an optimal sensing result.

Figure 11:
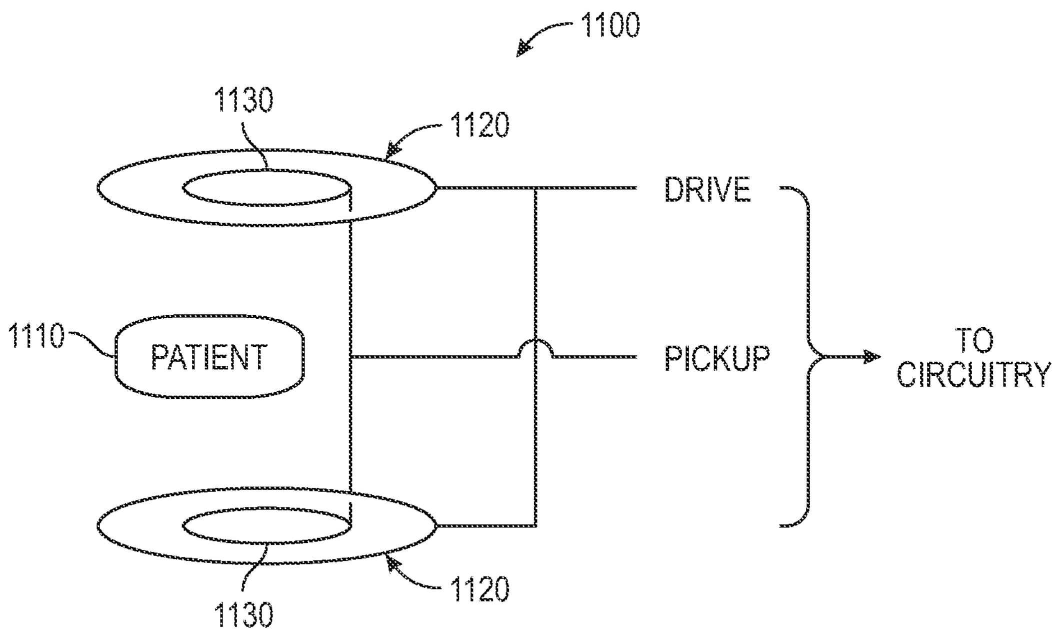
FIG. 11 is another embodiment of the system and method of FIG. 8, in which the driver and pickup coils thereof are arranged in a pair of opposing, coaxial assemblies on each of opposing sides of the patient's body for sensing NPs at relatively deep locations within the body.

Another embodiment for sensing a deep treatment/wound site is shown in the arrangement 1100 of FIG. 11. In this embodiment, the patient 1110 is interposed between a pair of opposing, coaxial coil arrangements, each consisting of an outer drive coil 1120 and an inner pickup coil 1130. The signals received from each pickup coil can be combined and/or compared using known techniques to derive appropriate sensed measurements. These are delivered to circuitry as described above.

IV. Conclusion

It should be clear that the above-described system and method for measuring and quantifying pain provides an effective and non-invasive technique for quantifying pain that can be compared to an absolute scale, thereby achieving desirable outcomes. The sensitivity of the system is such that microscopic probes can be used, limiting the potential for harm or discomfort to the patient. Moreover the system can be constructed and used in a manner that is inexpensive and portable.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. In general, the use of the system and method is directed toward human treatment, but can be beneficial in treating other lifeforms, such as a range of smaller and larger mammals. Also, as used herein the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A system for measuring pain level in a body at a site containing a predetermined concentration of magnetic nanoparticles comprising:

- a drive coil and a pickup coil that transmit and measure a field passing through the site based upon response of the magnetic nanoparticles; and
- a processor that computes a pain index corresponding to a degree of pain at the site, the pain index being determined from variations in measurements of magnetic nanoparticle behavior indicative of inflammation and pain biomarker concentration of the field.

2. The system as set forth in claim 1 wherein the processor derives values for levels of cytokine IL-6, SP and temperature at the site.

3. The system as set forth in claim 2 wherein the drive coil and pickup coil reside in a housing of a handheld sensing device.

4. The system as set forth in claim 3 wherein the processor resides in the housing.

5. The system as set forth in claim 4 wherein the drive coil and the pickup coil are arranged in a coaxial arrangement on a same side of the site.

6. The system as set forth in claim 1 wherein the drive coil and the pickup coil are arranged, respectively, at separate, remote locations relative to the site.

7. The system as set forth in claim 1 wherein the pickup coil comprises a pair of pickup coils located on each of opposing sides of the site and the drive coil comprises a pair of drive coils coaxial with respect of the pickup coils.

8. A method for measuring pain level in a body at a site containing a predetermined concentration of magnetic nanoparticles comprising the steps of:

operating a drive coil and a pickup coil with respect to the site so as to transmit and measure a field passing through the site based upon response of the magnetic nanoparticles; and computing a pain index corresponding to a degree of pain at the site, the pain index being determined from variations in measurements of magnetic nanoparticle behavior indicative of inflammation and pain biomarker concentration of the field.

9. The method as set forth in claim 8, further comprising, deriving values for levels of cytokine IL-6, SP and temperature at the site.

10. The method as set forth in claim 8, further comprising, locating the drive coil and pickup coil reside in a housing of a handheld sensing device and positioning the handheld device with respect to the body to measure the field at the site.

11. The method as set forth in claim 10, further comprising, performing the computing with a processor located in the housing.

12. The method as set forth in claim 8, further comprising, arranging the drive coil and the pickup coil in a coaxial arrangement on a same side of the site.

13. The method as set forth in claim 8, further comprising, arranging the drive coil and the pickup coil, respectively, at separate, remote locations relative to the site.

14. The method as set forth in claim 13, further comprising, arranging the pickup coil perpendicular to the drive coil.

15. The method as set forth in claim 14, further comprising, locating the pickup coil adjacent to a DC coil.

16. The method as set forth in claim 8, further comprising, linking a computing device, wired or wirelessly, with a that performs the step of computing, the computing device comprising a graphical user interface.

17. The method as set forth in claim 11, further comprising powering the processor with at least one of an on-board power supply; or a wall-current transformer.

18. The method as set forth in claim 17, further comprising, powering the on-board power supply with at least one battery.

19. The method as set forth in claim 8, further comprising, displaying results of the step of computing on a graphical user interface.

* * * * *